United States Patent
Park et al.

(10) Patent No.: US 10,832,452 B2
(45) Date of Patent: Nov. 10, 2020

(54) METHOD AND APPARATUS FOR GENERATING MAGNETIC RESONANCE IMAGE

(71) Applicant: KOREA ADVANCED INSTITUTE OF SCIENCE AND TECHNOLOGY, Daejeon (KR)

(72) Inventors: Hyun-wook Park, Daejun-si (KR); Hyun-seok Seo, Daejeon (KR)

(73) Assignee: KOREA ADVANCED INSTITUTE OF SCIENCE AND TECHNOLOGY (KR)

( * ) Notice: Subject to any disclaimer, the term of this patent is extended or adjusted under 35 U.S.C. 154(b) by 94 days.

(21) Appl. No.: 16/304,505

(22) PCT Filed: Apr. 21, 2017

(86) PCT No.: PCT/KR2017/004285
§ 371 (c)(1),
(2) Date: Nov. 26, 2018

(87) PCT Pub. No.: WO2017/204468
PCT Pub. Date: Nov. 30, 2017

(65) Prior Publication Data
US 2019/0139274 A1    May 9, 2019

(30) Foreign Application Priority Data
May 27, 2016 (KR) .................. 10-2016-0065340

(51) Int. Cl.
*G01V 3/00* (2006.01)
*G06K 9/00* (2006.01)
(Continued)

(52) U.S. Cl.
CPC ............ *G06T 11/006* (2013.01); *A61B 5/055* (2013.01); *A61B 5/7257* (2013.01);
(Continued)

(58) Field of Classification Search
USPC ........ 382/100, 103, 106–107, 128–134, 156, 382/162, 168, 173, 181, 199, 224, 232,
(Continued)

(56) References Cited

U.S. PATENT DOCUMENTS 9,188,655 B2   11/2015   Takeshima
9,213,075 B2   12/2015   Miyazaki et al.
(Continued)

FOREIGN PATENT DOCUMENTS

JP     2013240571 A     12/2013
WO    WO-2016017385 A1   2/2016

OTHER PUBLICATIONS

International Search Report (in English and Korean) and Written Opinion (in Korean) issued in PCT/KR2017/004285, dated Jul. 27, 2017; ISA/KR.

*Primary Examiner* — Seyed H Azarian
(74) *Attorney, Agent, or Firm* — Harness, Dickey & Pierce, P.L.C.

(57) ABSTRACT

A magnetic resonance imaging method and a magnetic resonance imaging apparatus using a parallel image reconstruction are disclosed. Some embodiments provide a magnetic resonance imaging apparatus including a receiving coil configured to receive a magnetic resonance (MR) signal through a plurality of channels, and an image information acquisition unit configured to acquire k-space data for each channel by undersampling an MR signal received from the receiving coil, and to perform an inverse Fourier transform on the k-space data for each channel, to generate a hybrid-space for each channel, and an image processing unit configured to apply a parallel image reconstruction, while sliding a unitary window to channel-by-channel hybrid-space data, within an area corresponding to the unitary window, and thereby reconstruct missing data.

15 Claims, 9 Drawing Sheets

(51) Int. Cl.
  *G06T 11/00* (2006.01)
  *A61B 5/055* (2006.01)
  *A61B 5/00* (2006.01)
  *G01R 33/56* (2006.01)
  *G01R 33/561* (2006.01)

(52) U.S. Cl.
  CPC ...... *G01R 33/5608* (2013.01); *G01R 33/5611* (2013.01); *A61B 2576/00* (2013.01)

(58) Field of Classification Search
  USPC ....... 382/254, 276, 286–291, 305, 312, 274; 600/420; 378/4, 21; 324/309
  See application file for complete search history.

(56) References Cited

U.S. PATENT DOCUMENTS

| | | |
|---|---|---|
| 9,245,321 B2 | 1/2016 | Park et al. |
| 2008/0231272 A1* | 9/2008 | Taniguchi ............ G01R 33/565 324/309 |
| 2008/0279433 A1 | 11/2008 | Brau et al. |
| 2009/0134872 A1 | 5/2009 | Brau et al. |
| 2013/0278256 A1 | 10/2013 | Ahmad et al. |
| 2013/0285655 A1 | 10/2013 | Miyazaki et al. |
| 2013/0285662 A1 | 10/2013 | Takeshima |
| 2014/0043026 A1* | 2/2014 | Frahm ................... G01R 33/48 324/309 |
| 2015/0108979 A1* | 4/2015 | Park ................... G01R 33/5611 324/309 |
| 2015/0117735 A1 | 4/2015 | Park et al. |
| 2015/0192653 A1* | 7/2015 | Sharif ................ G01R 33/4824 600/420 |
| 2017/0035298 A1* | 2/2017 | Contijoch ............ A61B 5/0044 |
| 2017/0200291 A1* | 7/2017 | Kamada ................ A61B 5/742 |

\* cited by examiner

Sensitivity map of each channel

METHOD AND APPARATUS FOR GENERATING MAGNETIC RESONANCE IMAGE

CROSS-REFERENCE TO RELATED APPLICATIONS

This application is a U.S. National Phase Application under 35 U.S.C. 371 of International Application No. PCT/KR2017/004285, filed on Apr. 21, 2017 and published in Korean as WO 2017/204468 A1 on Nov. 30, 2017, which claims priority under 35 USC § 119 (a) of Korean Patent Application No. 10-2016-0065340, filed on May 27, 2016. The disclosures of the above applications are incorporated herein by reference. Furthermore, this non-provisional application claims priority in countries, other than the U.S., with the same reason based on the Korean patent application, the entire content of which is hereby incorporated by reference.

TECHNICAL FIELD

The present disclosure in some embodiments relates to a magnetic resonance (MR) image generating method and a magnetic resonance imaging apparatus using a parallel image reconstruction.

BACKGROUND

The statements in this section merely provide background information related to the present disclosure and do not necessarily constitute prior art.

Magnetic resonance imaging is one of the imaging technologies using nuclear magnetic resonance principle. A human body is put in a magnetic resonance imaging apparatus that generates a magnetic field, generating a high frequency to cause the hydrogen nuclei of the body to resonate and to emit signals, the difference of which is measured and reconstructed into an image through a computer.

Magnetic resonance imaging apparatus has an advantage of obtaining images of various contrasts by controlling various parameters used in the image generation process. Clinical diagnosis requires images of multiple contrasts. However, since it takes a long time to capture an image, it troubles the patient, causing motions to occur spontaneously or involuntarily, resulting in image deteriorations. This has led to the development of several methods to shorten image acquisition time.

For increasing the speed of acquiring a magnetic resonance image in a conventional magnetic resonance imaging apparatus, there are a method of acquiring as many signals necessary for image generation as possible in a short time, and a method of omitting some of the process of obtaining data necessary for image generation.

The method of acquiring as many signals necessary for image generation as possible in a short time, includes gradient echo sequences for generating a signal by using only slice selection gradient during a short repetition time (TR), and an echo planar imaging (EPI) sequence that switches a gradient magnetic field during one TR, for acquiring multiple phases of encoding data at once.

The method of acquiring the most possible signals for image generation in a short time, heavily depends its performance on the hardware specification used and is greatly influenced by parameters such as TR or echo time (TE), which imposes a limitation upon the ability to obtain the image of a desired contrast.

The method of omitting some of the process of obtaining data necessary for image generation includes a parallel imaging method using multiple receiving coils. The parallel image reconstruction method is a method of intermittently performing sampling and acquiring data to reconstruct an image, instead of sampling in a k-space at a Nyquist ratio. By locating the magnetic resonance signal based on the positions and sensitivities of the multiple receiving coils which are already known, a lot of steps in the image acquisition process can be omitted. Although the imaging speed is improved with the parallel image reconstruction method, aliasing occurs in the image because the sampling rate does not satisfy the Nyquist rate, making it difficult to obtain a high resolution image. Restoration techniques for the image with such aliasing are represented by SENSitivity Encoding (SENSE) wherein reconstruction is performed in the image area and GeneRalized Auto-calibrating Partially Parallel Acquisitions (GRAPPA) wherein reconstruction is performed in the k-space area.

Parallel image reconstruction methods such as SENSE and GRAPPA exhibit excellent performance at a small acceleration ratio and have a short recovery time of missing data. However, they have a disadvantage of a sharp decline in the image quality at a high acceleration ratio due to the limitation of the coil sensitivity profile.

DISCLOSURE

Technical Problem

The present disclosure in some embodiments seeks to provide a method of improving image reconstruction performance even in a region of small autocalibration signal (ACS) and at a high acceleration ratio by optimizing the use of the spatial sensitivity of the receiving coil, and an apparatus using the method.

SUMMARY

At least one aspect of the present disclosure provides a magnetic resonance imaging apparatus including a receiving coil, an image information acquisition unit and an image processing unit. The receiving coil is configured to receive a magnetic resonance (MR) signal through a plurality of channels. The image information acquisition unit is configured to acquire k-space data for each channel by undersampling an MR signal received from the receiving coil, and to perform an inverse Fourier transform on the k-space data for each channel, to generate a hybrid-space for each channel. The image processing unit is configured to apply a parallel image reconstruction, while sliding a unitary window to channel-by-channel hybrid-space data, within an area corresponding to the unitary window, and thereby reconstruct missing data.

Another aspect of the present disclosure provides a method of generating a magnetic resonance (MR) image including receiving, by a receiving coil, an MR signal through a plurality of channels, and generating k-space data for each channel by undersampling the MR signal received from the receiving coil, and generating channel-by-channel hybrid-space data having both a k domain and a spatial domain by performing an inverse Fourier transform on the k-space data for each channel, and reconstructing missing data by applying a parallel image reconstruction, while sliding a unitary window to the channel-by-channel hybrid-space data, within an area corresponding to the unitary window, and generating channel-by-channel MR images by using channel-by-channel reconstructed data, and generating a final MR image based on the channel-by-channel MR images.

ADVANTAGEOUS EFFECTS

As described above, one aspect of the present disclosure effects improved performance of the parallel image reconstruction method when employed in the MR image generation process, by optimizing the use of receiving coil sensitivity.

A few further steps of the present disclosure to the conventional parallel image reconstruction method in operation, outperforms such conventional method even with less ACS lines or at a high acceleration ratio, resulting in shortened MR image generation time.

DETAILED DESCRIPTION

Figure 1:
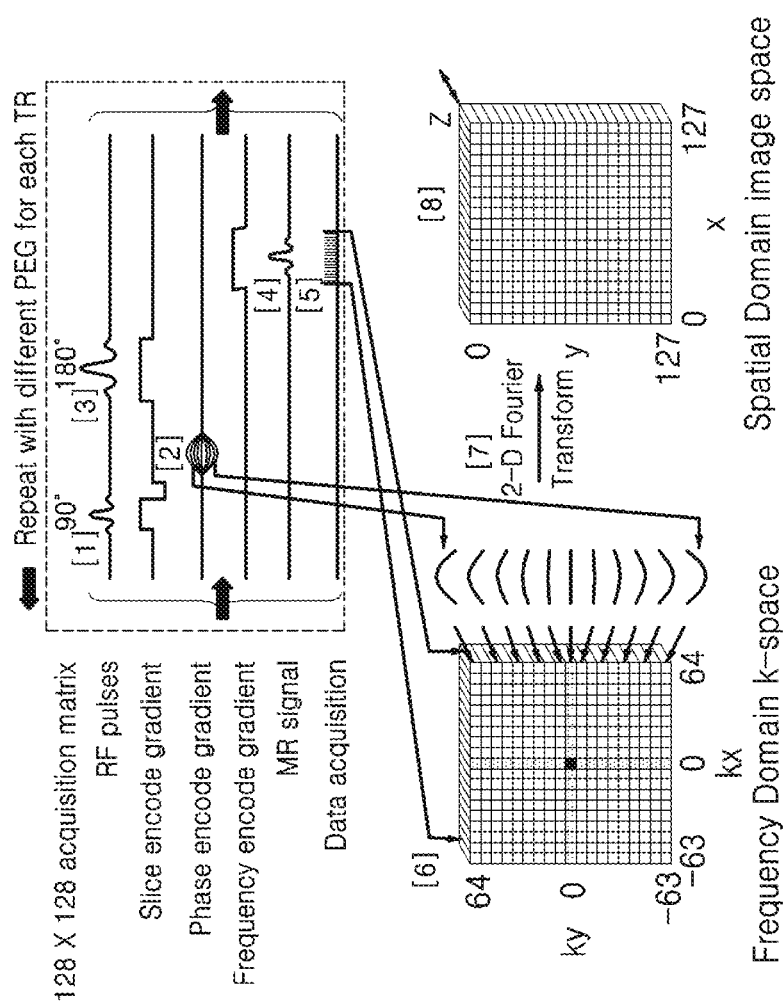
FIG. 1 is a diagram for explaining a process of acquiring a magnetic resonance image (MRI) by using a magnetic field, a slice selection gradient, a magnetic resonance (MR) signal and k-space.

Hereinafter, some embodiments of the present disclosure will be described in detail with reference to the accompanying drawings. In the following description, like reference numerals designate like elements, although the elements are shown in different drawings. Further, in the following description of some embodiments, a detailed description of known functions and configurations incorporated therein will be omitted for the purpose of clarity and for brevity.

Additionally, various terms such as first, second, A, B, (a), (b), etc., are used solely for the purpose of differentiating one component from the other, not to imply or suggest the substances, the order or sequence of the components. Throughout this specification, when a part "includes" or "comprises" a component, the part is meant to further include other components, not excluding thereof unless specifically stated to the contrary. The terms such as "unit," "module," and the like refer to units for processing at least one function or operation, which may be implemented by hardware, software, or a combination thereof.

FIG. 1 is a diagram for explaining a process of acquiring a magnetic resonance image (MRI) by using a magnetic field, a slice selection gradient, a magnetic resonance (MR) signal and k-space.

The following describes with reference to FIG. 1, a spatial encoding process for acquiring an MR image by using an MR signal, and an MR imaging process.

MRI imaging is the process of generating images by receiving MR signals from protons distributed in the human body, which is a three dimensional space. Information on the position and the signal intensity of the proton is processed and imaged by a computer. Such imaging needs measurements of the position of the proton and the intensity of the signal in relation to the position. For measurement, a main magnetic field is applied to the human body, and an additional slice selection gradient is applied to the main magnetic field. Most MRI equipment forms a main magnetic field along the long axis of the human body, and this orientation is usually represented by z-axis. When the oblique magnetic field is applied to the z-axis, the intensity of the magnetic field changes depending on positions in the human body. In this case, a single RF signal applied causes an emission of signal of only one proton out of the body section at the same site. Analyzing the signal of the proton located in that section determined provides an MR signal, with the intensity of the MR signal being expressed in contrast with respect to the RF signal.

With all of the proton signals located in the cross section adding up to a single combined signal, each proton is subjected to a spatial encoding process so as to distinguish x-axis position information from y-axis position information. Spatial encoding expresses two directions of an x-axis and y-axis in a two-dimensional space by using two encoding processes of phase encoding and frequency encoding. Hereinafter, it is assumed that the direction of the y-axis (the vertical direction of the cross section) is the phase encoding direction and the direction of the x-axis (the horizontal direction of the cross section) is the frequency encoding direction.

K-space has a spatial frequency domain and is formed by a kx-axis corresponding to frequency encoding and a ky-axis corresponding to phase encoding. The k-space is different from the actual physical space, but is represented in the drawings by a rectangular plane with an x-axis and a y-axis for easy understanding. The signal is obtained several times while changing the phase encoding gradient, to obtain position information in the ky-axis direction of the k-space. Meanwhile, a frequency encoding gradient is applied to extract the magnitude of signal intensity for each frequency, to obtain position information in the kx-axis direction. By performing two-dimensional Fourier transform (2DFT) on the k-space region, a magnetic resonance image is obtained.

Figure 2:
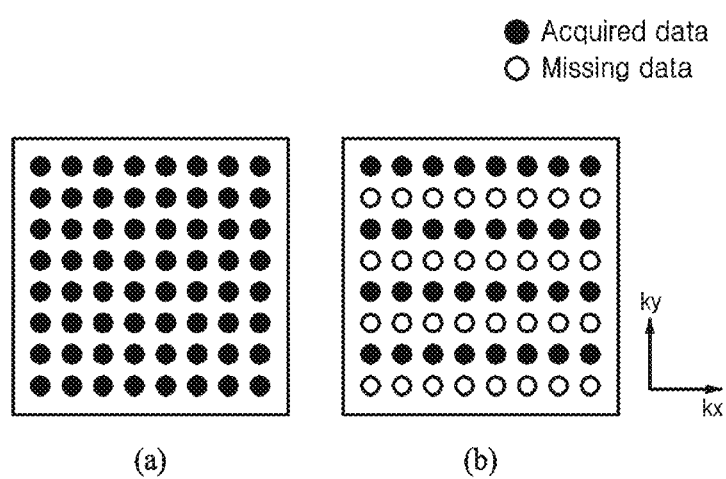
FIG. 2 is a diagram for explaining sampling in k-space according to at least one embodiment of the present disclosure.

FIG. 2 is a diagram for explaining sampling in k-space according to at least one embodiment of the present disclosure. FIG. 2 shows at (a) a case where a signal is fully sampled, and at (b) a case where a signal is under-sampled.

The following describes, with reference to FIG. 2, a method of sampling k-space and acquiring data where a parallel image reconstruction method is applied, to shorten the time for generating an MR image.

K-space data is obtained by sampling the MR signal received by the receiving coil. Therefore, reduced time in this sampling process can quicken the MR image generation.

The first case to discuss is full sampling of a signal with reference to FIG. 2 at (a). Full sampling is a sampling method in which a signal is sampled to satisfy a Nyquist rate, which allows the image to be recovered without loss.

However, this needs the entire k-space area to be closely sampled, which takes longer time for sampling, resulting in a longer time for generating an MR image. Here, the number of samples is assumed to be N.

Next, the case of undersampling the signal when applying the parallel image reconstruction method will be described with reference to FIG. 2 (b). FIG. 2 at (b) illustrates a case where data is undersampled in the ky-axis direction by undersampling in phase encoding of an MR signal. When data is undersampled in the ky-axis direction, data acquisition in the ky-direction is accelerated. Undersampling is to sample the signal at a lower rate than a Nyquist rate where, with the number of sampling being $N_P$, the data acquisition time may be $R_P=N/N_P$ times faster. However, sampling not performed at the Nyquist rate causes an aliasing phenomenon to occur. The aliasing phenomenon refers to one in which images show overlapped when generated after being converting into a spatial domain. In parallel image reconstruction method, aliasing phenomenon can be eliminated by performing appropriate processing using additional data measured through a multi-channel coil.

At least one embodiment of the present disclosure uses a method of sampling (under sampling) at a rate lower than the Nyquist rate and acquiring data of the k-space in the process of shortening the MR image generation time by applying the parallel image reconstruction method. The drawing illustrates a case of sampling done in the ky-axis direction where $N_P=N/2$, although the present disclosure is not necessarily limited thereto. The present disclosure encompasses other conditions such as $N_P=N/3$, $N_P=N/4$, and any undersampling methods including undersampling at an irregular interval, to which the parallel image reconstruction method is applicable.

Figure 3A:
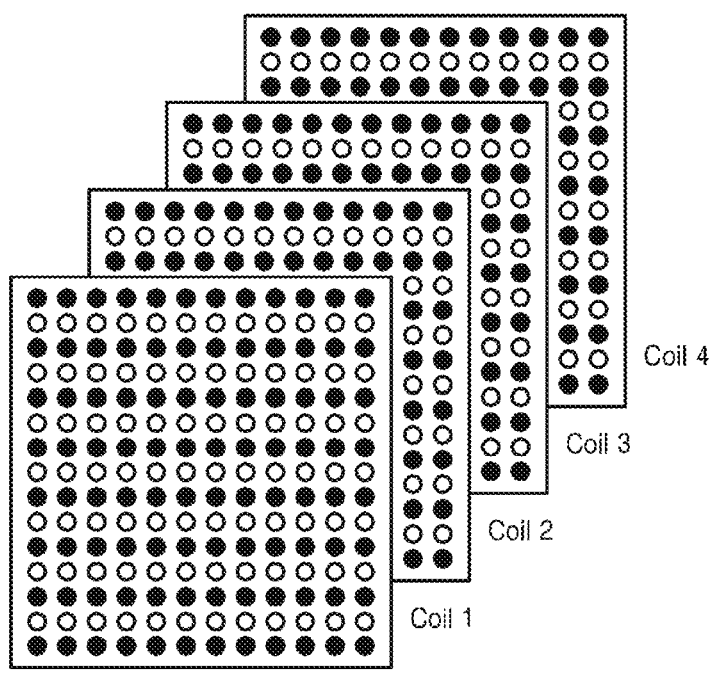
FIGS. 3A to 3C are diagrams for explaining GRAPPA, which is a parallel image reconstruction method used in at least one embodiment of the present disclosure.
Figure 3B:
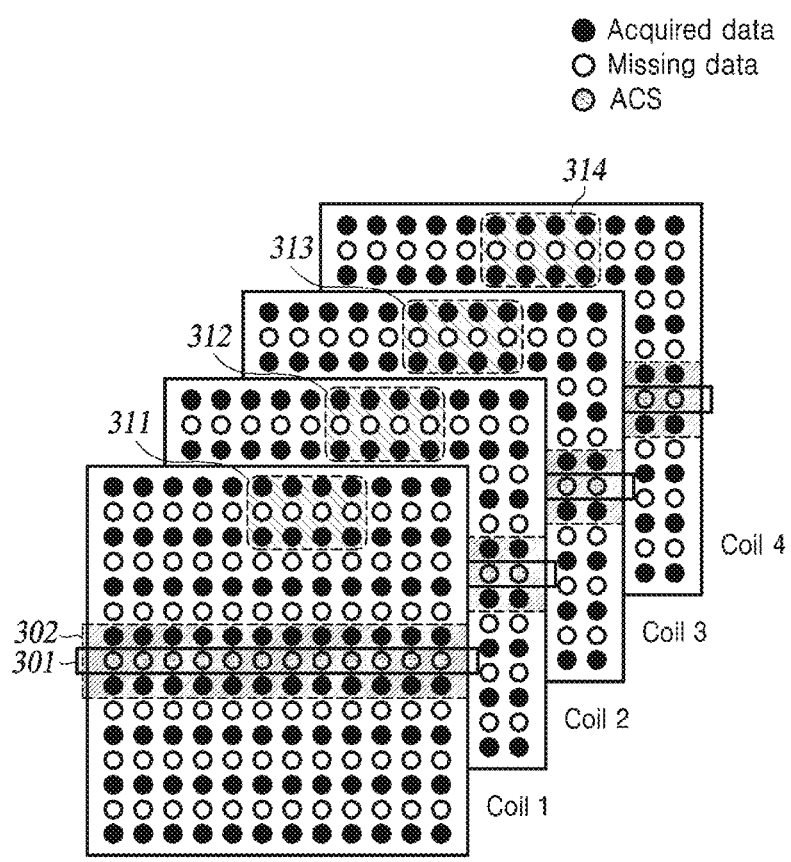
Figure 3C:
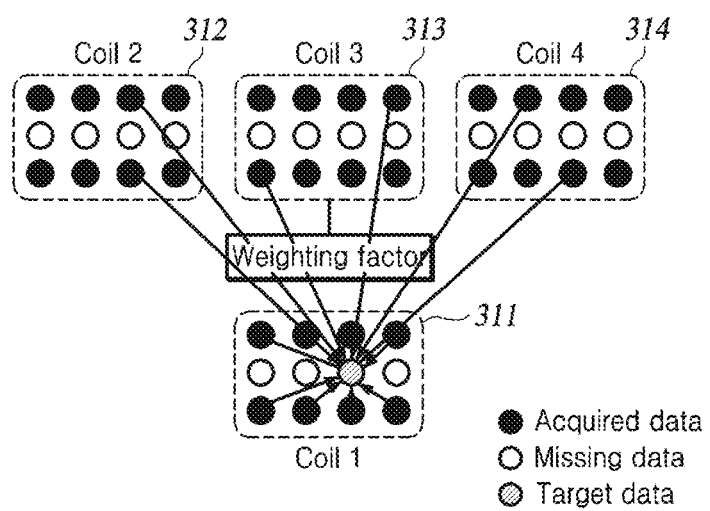

FIGS. 3A to 3C are diagrams for explaining GRAPPA, which is a parallel image reconstruction method used in at least one embodiment of the present disclosure. FIG. 3A illustrates channel-by-channel k-space data obtained by undersampling an MR signal in each channel of the receiving coil. FIG. 3B illustrates autocalibration signal (ACS) lines, ACS areas, and filter kernels in k-space data for each channel. FIG. 3C illustrates a method of restoring missing data of k-space through GRAPPA.

In FIGS. 3A to 3C, the number of channels of the receiving coil is assumed to be four, showing an example case of accelerating data acquisition in the ky-direction.

When undersampling in order to reduce the MRI generation time, the k-space data area has missing data remained unacquired. The GRAPPA parallel image reconstruction method is adapted to reconstruct such missing data. Specifically, it is a process of removing an aliasing phenomenon by using an ACS area.

As described with reference to FIG. 2, the MR signals are undersampled to fill the k-space for each channel. As shown in FIG. 3A, since the undersampling has omitted an encoding process, the k-space data area has missing data remained unacquired.

In addition thereto, an ACS line 301 is fully sampled in k-space for each channel to obtain data. As a result, a full-sampled ACS area 302 is formed in the k-space data, as in FIG. 3B. A weighting factor of each coil is calculated from information of each ACS area 302 of undersampled k-space data obtained from all channels of the receiving coil. The weighting factor is the calculated value of any possible effects of each channel coil on the spatial frequency in the entire k-space data, the value being calculated from the obtained data, and reflecting the spatial interaction of the channel coil.

As shown in FIG. 3C, missing data is estimated by using the weighting factor of each coil and the data acquired for each channel coil. At this time, GRAPPA uses all the k-space data obtained through the plurality of channels of the receiving coil, to estimate target missing data in one channel of the receiving coil. To restore the missing data, blocks or kernels 311, 312, 313 and 134 in a certain area are designated, and all acquired data information included in those blocks or kernels 311, 312, 313 and 134 are used for estimating the missing data.

FIG. 3C seems to show only the partial data of the kernels 312, 313 and 134 of coil 2, coil 3 and coil 4 is used to recover the missing data, just for the sake of convenience, but the missing data is actually estimated by using all the acquired data included in the kernels 311, 312, 313 and 314 of the coil 1 through coil 4. In addition, FIG. 3B shows an example case of estimating missing data by using filter kernels in a part of the k-space, although a wider range or a narrower range of blocks or kernels can also be used to estimate missing data.

With all missing data estimated to fill the k-space and to generate an MR image, aliasing is removed from the MR image for each channel. Then, the MR images of the respective channels are combined to obtain the final image.

During undersampling the MR signal and applying the parallel image reconstruction method to shorten the time for generating the MR image, reflecting the spatial sensitivity of the receiving coil can enhance accurate estimation in the process of estimating the missing data. At least one embodiment of the present disclosure provides a method of improving the performance of the parallel image reconstruction method through optimizing the use of the spatial sensitivity of the receiving coil by applying window sliding that reflects the sensitivity of the receiving coil, so as to obtain enhanced image reconstruction and a high acceleration ratio even with a small ACS area used.

Figure 4:
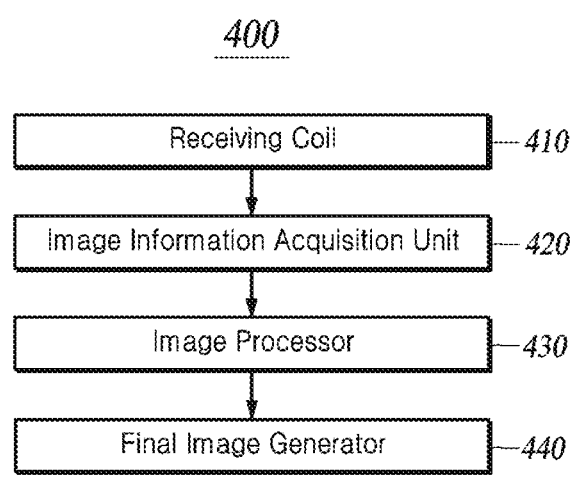
FIG. 4 is a schematic block diagram of the components of a magnetic resonance imaging apparatus according to at least one embodiment of the present disclosure.

FIG. 4 is a schematic block diagram of the components of a magnetic resonance imaging apparatus according to at least one embodiment of the present disclosure.

Figure 5:
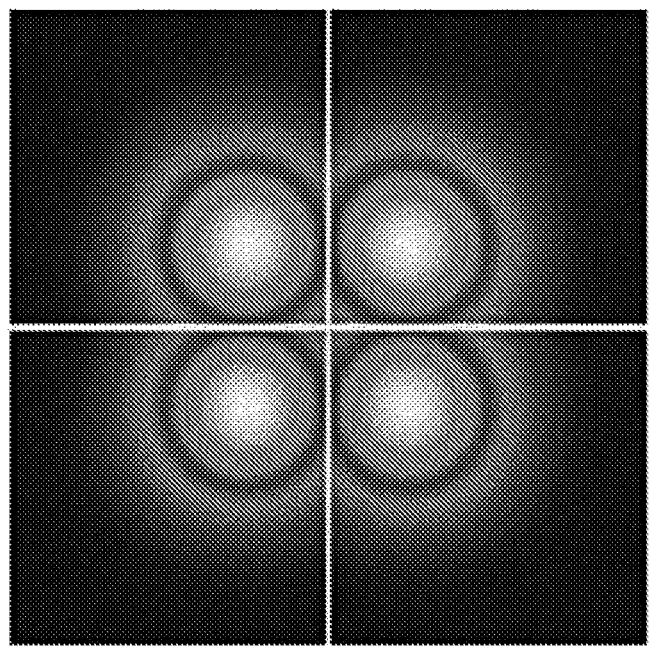
FIG. 5 is a diagram of the sensitivities of the respective channels of a receiving coil.

FIG. 5 is a diagram of the sensitivities of the respective channels of a receiving coil.

Figure 6:
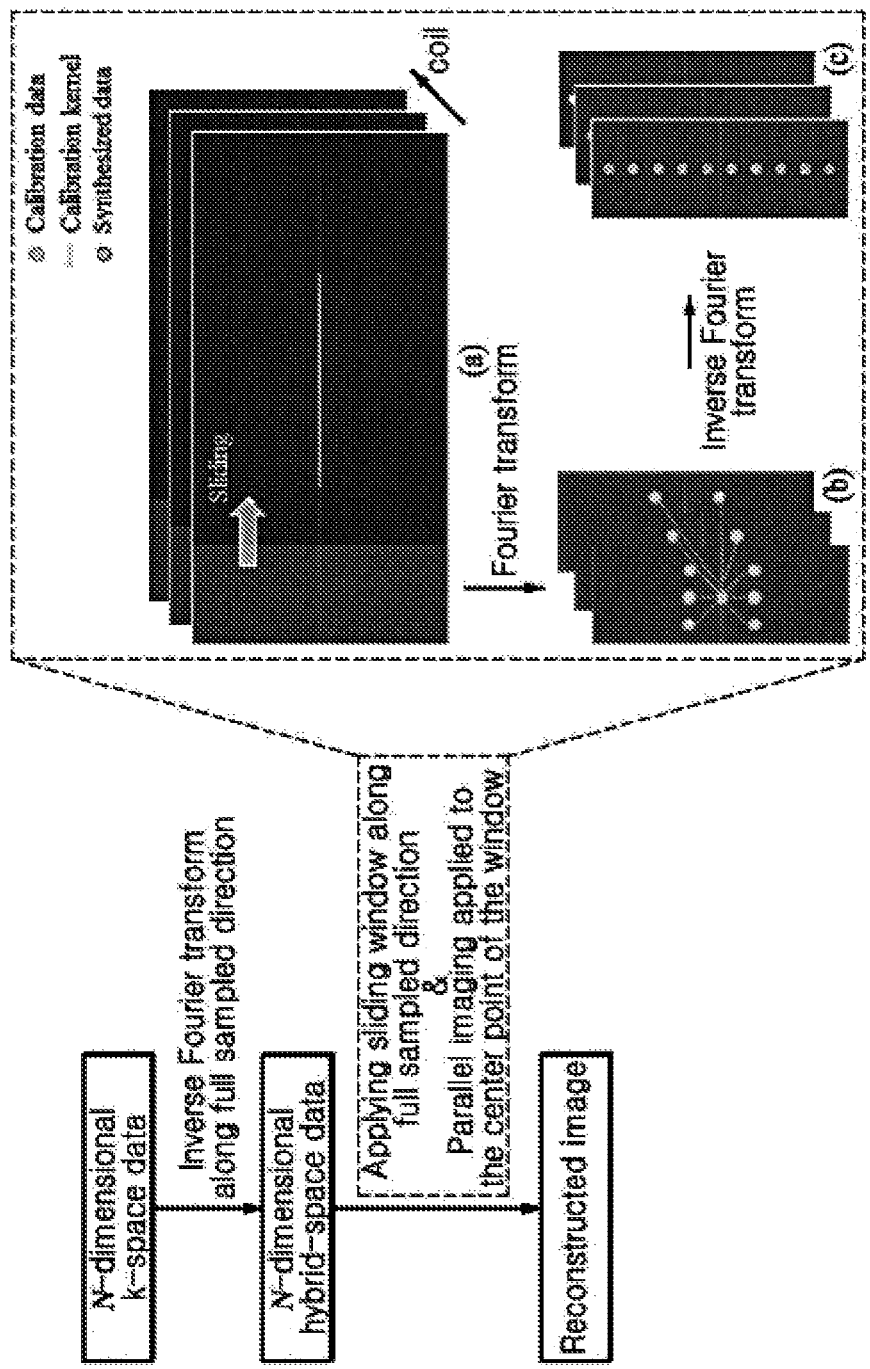
FIG. 6 is a diagram of the operation of an image information acquisition unit and an image processing unit of an MR imaging apparatus according to at least one embodiment of the present disclosure.

FIG. 6 is a diagram of the operation of an image information acquisition unit and an image processing unit of an MR imaging apparatus according to at least one embodiment of the present disclosure.

Hereinafter, the components of the MR imaging apparatus according to embodiments of the present disclosure and the functions of the respective components will be described with reference to FIGS. 4, 5 and 6.

Referring to FIG. 4, the MR imaging apparatus 400 is an apparatus for generating an MR image by using MR signals obtained from a plurality of channel coils of a receiving coil 410.

The MR imaging apparatus 400 may include the receiving coil 410, an image information acquisition unit 420, an image processing unit 430, and a final image generating unit 440. The image information acquisition unit 420 may be wired or wirelessly connected to the receiving coil 410.

The receiving coil 410 includes a plurality of channel coils. The receiving coil 410 includes first through n-th channel coils, and each of the n channel coils receives an MR signal, which is a high frequency (RF) signal.

Specifically, the receiving coil 410 applies a magnetic field to a target object to acquire an MR image, and applies an RF signal to cause a nucleus of the target object to emit an MR signal. The energy emitted from the nuclear spin due to the magnetic field becomes an MR signal having the RF signal form. The receiving coil 410 detects and transmits the emitted MR signal to the image information acquisition unit 420.

The image information acquisition unit 420 receives the MR signal acquired by the receiving coil 410. The image information acquisition unit 420 obtains k-space data for each channel based on the MR signal received by each channel of the receiving coil 410. The MR signal undergoes a spatial encoding process by the magnetic field applied by the receiving coil 410, and includes information on positions along the ky-axis and kx-axis directions. The image information acquisition unit 420 may utilize the information on positions along the ky-axis and kx-axis directions for arranging, in the k-space, the MR signals received respectively from the n channel coils included in the receiving coil 410, and thereby generating n pieces of k-space data.

The image information acquisition unit 420, as described with reference to FIG. 2, may under-sample the MR signal received from each of the plurality of channel coils to obtain undersampled k-space data corresponding to each of the plurality of channel coils. Here, the undersampled k-space data includes a plurality of acquired line data. In addition, in order to apply the parallel image reconstruction method, data items may be acquired by full-sampling the ACS lines in the k-space for each channel. As a result, the image information acquisition unit 420 may obtain undersampled k-space data having an ACS area. The undersampled k-space data is insufficient to generate the channel reconstructed image. Therefore, missing data not recovered in the under-sampling process is subsequently reconstructed by using the parallel image reconstruction method.

Obtaining k-space data by undersampling the MR signal by the image information acquisition unit 420 may be undersampling performed at a rate lower than the Nyquist rate for a certain direction of the k-space. Here, the certain direction may be the phase encoding direction which is the ky-direction of the k-space, but is not limited thereto.

FIG. 6 shows the process after acquisition of k-space data. The flow chart on the left side of FIG. 6 schematically shows sequential operations of the image information acquisition unit 420 and the image processing unit 430. The right side of FIG. 6 specifically shows the window sliding performed by the image processing unit 430.

The image information acquisition unit 420 performs inverse Fourier transform on the k-space data in the direction of the full sampling performed, to generate hybrid-space data. The image processing unit 430 generates a reconstructed image by reconstructing middle pixels of the window area, by applying a parallel image reconstruction method, while sliding the window along the direction of the full sampling performed, to the generated hybrid-space data.

The image information acquisition unit 420 transforms k-space data for each channel into hybrid-space data for each channel. Hybrid-space data refers to data obtained by performing inverse Fourier transform of k-space data in a certain direction. The hybrid-space data is maintained in the k domain in the direction in which the inverse Fourier transform is not performed, and is transformed into the spatial domain in the direction in which the inverse Fourier transform is performed. The k-space data is expressed using the frequency and phase information of the received MR signal, and the information on the spatial sensitivity map of the receiving coil as shown in FIG. 5 is not reflected in the k-space. Therefore, in order to reflect the spatial sensitivity map of the receiving coil, k-space data is made to undergo inverse Fourier transform in a certain direction, to be transformed into hybrid-space data. Since the hybrid-space data has a spatial domain in the direction in which the inverse Fourier transform is performed, the k-space data transformed becomes data reflecting the spatial sensitivity map of the receiving coil. The spatial sensitivity maps of the respective channels of the receiving coil are different for each channel of the receiving coil and for each channel coil space, as illustrated in FIG. 5. The spatial sensitivity maps of the receiving coil have different values depending on the relevant receiving coil used in the MRI apparatus.

The image information acquisition unit 420 may perform inverse Fourier transform on the k-space data in a direction that was not undersampled, to obtain channel-by-channel hybrid-space data. This results in the spatial sensitivity map of the receiving coil being reflected in undersampled directions, that is, directions in which data acquisition was not accelerated or in a fully sampled direction. The direction in which the data acquisition is not accelerated is the direction in which data is acquired by full sampling the MR signal, so aliasing will not issue in that direction even if the inverse Fourier transform is performed.

For example, when the data acquisition in the ky-direction is accelerated but not in the kx-direction, that is, when the under-sampling is performed only in the phase encoding process, the image information acquisition unit 420 performs the inverse Fourier transform on the acquired channel-by-channel k-space data in the kx-direction. FIG. 6 shows at (a) channel-by-channel hybrid-space data in which the spatial sensitivity map of the receiving coil is reflected by performing inverse Fourier transform in the kx-direction of the channel-by-channel k-space data. The k domain remains in the ky-direction in which data acquisition was accelerated, while transform into the spatial domain is performed in the kx-direction in which data acquisition was not accelerated.

In the drawing, the k-space and the hybrid-space are expressed as 2D regions and the data acquisition is accelerated in a certain axial direction of the k-space. However, the image information acquisition unit 420 may acquire channel-by-channel hybrid-space data by transforming the channel-by-channel k-space data it obtained, along not only the ky-axis or kx-axis direction, but also all directions in which data acquisition was not accelerated, i.e., in all directions in which no under-sampling was performed.

The image processor 430 reconstructs missing data by applying parallel image reconstruction to the channel-by-channel hybrid-space data. For the application of a parallel image reconstruction method, some embodiments uses an application method that while sliding a unitary window of a predetermined size to the channel-by-channel hybrid-space data, applies the parallel image reconstruction to an area corresponding to the unitary window.

Hereinafter, window sliding will be described in detail with reference to FIG. 6.

FIG. 6 shows at (a) the channel-by-channel hybrid-space data in which the spatial sensitivity map of the receiving coil is reflected by performing inverse Fourier transform in the kx-direction of the channel-by-channel k-space data. Generally, the sensitivity of the receiving coil is inversely proportional to the square of the spatial distance, and therefore the spatial sensitivity maps of coils, which are included in other data items than from the selected window area in FIG. 6 at (a), do not significantly affect the data of the selected window area. Rather, active noise may directly result from spatial information of other data than from the selected window area that is selected in the process of being reconstructed in the unitary window area. Therefore, at least one embodiment of the present disclosure applies the parallel image reconstruction method is only to the data in the window as shown in FIG. 6 (b), in order to exclude spatial information of data far from the window area. With useless sensitivity information of the receiving coils being excluded in the spatial domain, the occurrence of errors can be suppressed in image reconstruction.

The sliding direction of the window is the spatial domain direction of the hybrid-space domain data, that is, the direction in which no data acquisition acceleration has been done (in which full sampling was performed). The sliding can be made at arbitrarily set pixel intervals. When sliding at an interval of one pixel, all the pixels to be reconstructed can be taken into consideration, so that the highest performance can be achieved. FIG. 6 illustrates the sliding direction of the window to be the kx-direction, although the window sliding can proceed in all directions in which data acquisition was not accelerated, i.e., in all directions in which no under-sampling was performed.

The size of the unitary window may be determined according to the sensitivity of the MRI system and the receiving coil used by the system. The smaller the unitary window size, the smaller the data amount becomes for estimating missing data, which increases the error of estimation, but increasingly excludes useless information of the receiving coil in the window.

The image processor 430 reconstructs the missing data by using only the data of the area corresponding to the unitary window, and generates the reconstructed hybrid-space data for each channel. Specifically, as shown in FIG. 6 (b), the image processing unit 430 performs 1-D Fourier transform on an area corresponding to a unitary window to transform it into k-space. Then, the parallel image reconstruction method is applied to the unitary window area transformed into the k-space. When GRAPPA described in FIGS. 3A to 3C is applied to recover the missing data, all processes are performed in the area corresponding to the unitary window, including a calculation of the weight factor of each channel coil by using the ACS area, and estimation of missing data by using the filter kernels. Transformed into the k-space, the unitary window area, which is different from the k-space data acquired by the image information acquisition unit 420, with the unitary window applied thereto, amounts to data cleared of spatial information of data far from the window area, and helps to provide more accurate estimation of the missing data.

The image processor 430 may generate the channel-by-channel reconstructed hybrid-space data by using only the middle pixels in the unitary window area from the result of applying the parallel image reconstruction method. All the missing data in the unitary window are restored, and the inverse Fourier transform is performed on the area corresponding to the unitary window, to convert it into the hybrid-space. As shown in FIG. 6 at (c), only the middle pixels of the unitary window area re-transformed into the hybrid-space are used as the reconstructed hybrid-space data for each channel. When the window is slid at an interval of 1 pixel which is the minimum interval, the interval of the reconstructed data in the window area is also 1 pixel, which provides the entire hybrid-space data. Through applying the parallel image reconstruction method in this way, the quality of the image can be maintained even at a high acceleration ratio by excluding the receiving coil sensitivity information of the data area, which can act as noise.

At this time, the applied parallel image reconstruction method may be a method of reconstructing missing data in k-space by using ACS lines. For example, applicable methods include GRAPPA, iTerative Self-consistent Parallel Imaging Reconstruction (SPIRiT) and Efficient L1SPIRiT Reconstruction (eSPIRiT) among others.

As a result of applying the parallel image reconstruction method, the image processing unit 430 generates reconstructed hybrid-space data for each channel in which missing data is reconstructed for each channel, and transforms the data to generate an MR image for each channel coil. With all the missing data being reconstructed, an MR image can be obtained in which aliasing phenomenon is removed for each channel.

The image processor 430 may generate a plurality of channel-by-channel MR images by spatially transforming a plurality of channel-by-channel reconstructed hybrid-space data corresponding respectively to the plurality of channel coils. Specifically, through inverse Fourier transform of a plurality of channel-by-channel reconstructed hybrid-space data corresponding respectively to the plurality of channel coils, to perform a frequency-to-space transform operation thereof, a plurality of channel-by-channel MR images may be generated.

The final image generating unit 440 may generate a final MR image by using a plurality of channel-by-channel MR images. More specifically, multiple channel-by-channel MR images may be synthesized to generate a final MR image. For example, the image processing unit may obtain a final MR image by calculating the sum of squares or complex sum of multiple channel-by-channel MR images.

Figure 7:
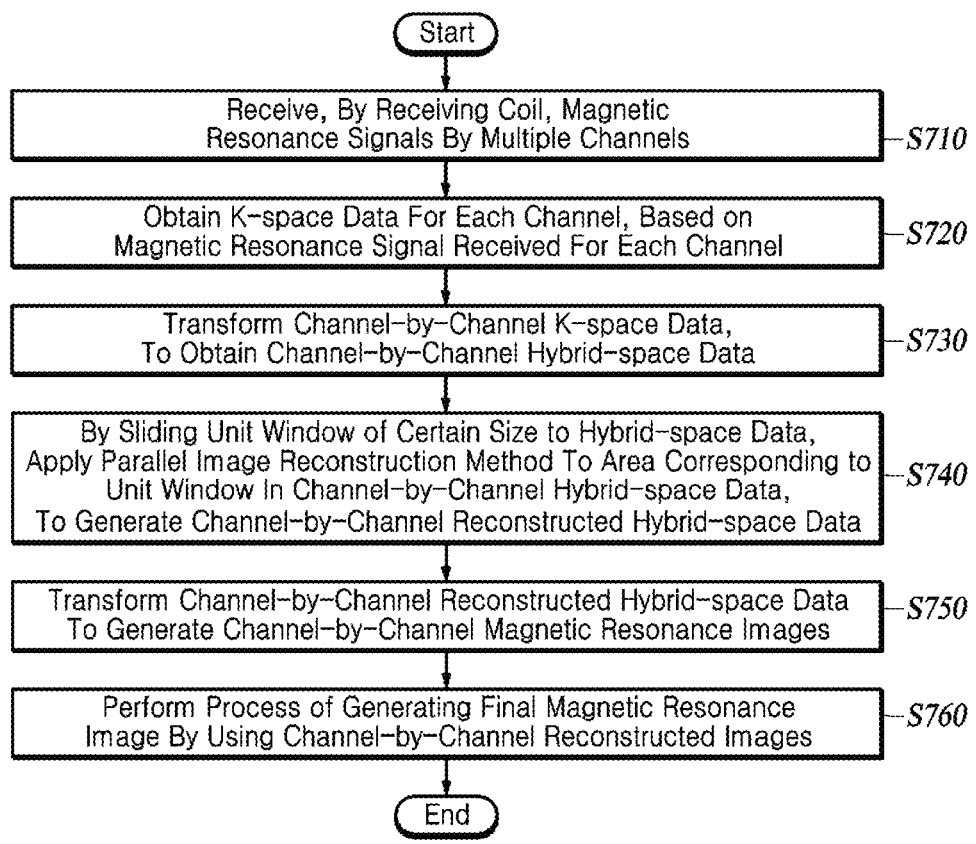
FIG. 7 is a flowchart of a method of generating an MR image according to at least one embodiment of the present disclosure.

FIG. 7 is a flowchart of a method of generating an MR image according to at least one embodiment of the present disclosure.

First, the receiving coil receives an MR signal by a plurality of channels (S710). The receiving coil includes first through n-th channel coils, each receiving an MR signal.

Then, k-space data for each channel is acquired by using the MR signal received through each channel of the receiving coil (S720). N pieces of k-space data are obtained by arranging the MR signals received at the respective n channel coils included in the receiving coil in the k-space by using information on the position in the ky-axis and kx-axis directions. In addition, undersampling the MR signals received respectively from the multiple channel coils can obtain undersampled k-space data corresponding respectively to the multiple channel coils. The undersampling of the MR signals to obtain k-space data may be undersampling at a rate lower than the Nyquist rate for a certain direction of k-space.

Subsequently, channel-by-channel k-space data are transformed into channel-by-channel hybrid-space data (S730). Channel-by-channel spatial data may be obtained by performing inverse Fourier transform on the k-space data in a direction in which no undersampling was performed. This process is for reflecting the spatial sensitivity map of the receiving coil. Channel-by-channel hybrid-space data may be obtained by transforming the channel-by-channel k-space data in all directions in which data acquisition was not accelerated.

Next, in step S740, while sliding a unitary window of a predetermined size to the channel-by-channel hybrid-space data, the parallel image reconstruction is applied to an area corresponding to the unitary window, to generate channel-by-channel reconstructed hybrid-space data. The sliding direction of the window corresponds to the spatial domain direction of the hybrid-space domain data, i.e., the direction in which data acquisition was not accelerated.

Next, the channel-by-channel reconstructed hybrid-space data are transformed to generate channel-by-channel reconstructed images (S750). Since all the missing data are reconstructed, an MR image can be obtained in which aliasing phenomenon is removed for each channel. Specifically, through inverse Fourier transform of a plurality of reconstructed hybrid-space data corresponding respectively to the plurality of channel coils, to perform a frequency-to-space transform operation thereof, a plurality of channel-by-channel MR images may be generated.

The channel-by-channel reconstructed images are used to generate a final MR image (S760). More specifically, multiple channel-by-channel MR images may be synthesized to generate a final MR image. For example, the image processing unit may obtain a final MR image by calculating the sum of squares or complex sum of multiple channel-by-channel MR images.

Although exemplary embodiments of the present disclosure have been described for illustrative purposes, those skilled in the art will appreciate that various modifications, additions and substitutions are possible, without departing from the idea and scope of the claimed invention. Therefore, exemplary embodiments of the present disclosure have been described for the sake of brevity and clarity. The scope of the technical idea of the present embodiments is not limited by the illustrations. Accordingly, one of ordinary skill would understand the scope of the claimed invention is not to be limited by the above explicitly described embodiments but by the claims and equivalents thereof.

As described above, the magnetic resonance imaging method described in FIG. 7 can be implemented by a program and recorded on a computer-readable recording medium. The computer-readable recording medium on which the program for implementing some embodiments of the present disclosure are recorded includes all kinds of recording devices on which data that can be read by a computer system are recordable. Examples of the computer-readable recording medium include ROM, RAM, CD-ROM, magnetic tape, floppy disk, optical data storage, etc., and they are also implemented in the form of a carrier wave (e.g., transmission over the Internet). Further, the computer-readable recording medium can be distributed in computer systems connected via a network, wherein computer-readable codes can be stored and executed in a distributed mode. Functional programs, codes, and code segments for implementing embodiments of the present disclosure may be easily inferred by programmers skilled in the art to which the embodiments belong.

The invention claimed is:

1. A magnetic resonance imaging apparatus, comprising:
a receiving coil configured to receive a magnetic resonance (MR) signal through a plurality of channels;
an image information acquisition system configured to acquire k-space data for each channel by undersampling an MR signal received from the receiving coil, and to perform an inverse Fourier transform on the k-space data for each channel, to generate a hybrid-space for each channel;
an image processor configured to apply a parallel image reconstruction, while sliding a unitary window to channel-by-channel hybrid-space data, within an area corresponding to the unitary window, and thereby reconstruct missing data; and
wherein the image processor is configured to slide the unitary window at pixel intervals arbitrarily set in the channel-by-channel hybrid-space data.

2. The magnetic resonance imaging apparatus of claim 1, wherein the image processor is configured to slide the unitary window in a spatial domain direction of the channel-by-channel hybrid-space data.

3. The magnetic resonance imaging apparatus of claim 1, wherein the image processor is configured to reconstruct the missing data by exclusively using a middle pixel of a result of applying the parallel image reconstruction in the area corresponding to the unitary window.

4. The magnetic resonance imaging apparatus of claim 1, wherein the image processor is configured to generate the channel-by-channel hybrid-space data by performing an inverse Fourier transform on the k-space data for each channel in a direction in which no undersampling was performed.

5. The magnetic resonance imaging apparatus of claim 1, wherein the image information acquisition system is configured to acquire the k-space data for each channel by undersampling the MR signal at a rate lower than a Nyquist rate for any one direction of a k-space.

6. The magnetic resonance imaging apparatus of claim 1, wherein the image information acquisition system is configured to acquire the k-space data for each channel by undersampling the MR signal in a phase encoding direction of a k-space.

7. The magnetic resonance imaging apparatus of claim 1, wherein the image processor is configured to determine a magnitude of the unitary window according to a sensitivity of the receiving coil.

8. The magnetic resonance imaging apparatus of claim 1, wherein the image information acquisition system is configured to generate the channel-by-channel hybrid-space data by performing an inverse Fourier transform on the k-space data for each channel in all directions in which no undersampling was performed.

9. The magnetic resonance imaging apparatus of claim 1, wherein the image processing system is configured to apply one of GeneRalized Auto-calibrating Partially Parallel Acquisitions (GRAPPA), iTerative Self-consistent Parallel Imaging Reconstruction (SPIRiT), and Efficient L1SPIRiT Reconstruction (eSPIRiT) as the parallel image reconstruction.

10. A method of generating a magnetic resonance (MR) image, the method comprising:
receiving, by a receiving coil, an MR signal through a plurality of channels;
generating k-space data for each channel by undersampling the MR signal received from the receiving coil;
generating channel-by-channel hybrid-space data having both a k domain and a spatial domain by performing an inverse Fourier transform on the k-space data for each channel;
reconstructing missing data by applying a parallel image reconstruction, while sliding a unitary window to the channel-by-channel hybrid-space data, within an area corresponding to the unitary window;
generating channel-by-channel MR images by using channel-by-channel reconstructed data;
generating a final MR image based on the channel-by-channel MR images; and
wherein the image processor is configured to slide the unitary window at pixel intervals arbitrarily set in the channel-by-channel hybrid-space data.

11. The method of claim 10, wherein the generating of the k-space data for each channel comprises:
generating the k-space data for each channel by undersampling the MR signal at a rate lower than a Nyquist rate for any one direction of a k-space.

12. The method of claim 10, wherein the generating of the channel-by-channel hybrid-space data comprises:

performing the generating of the channel-by-channel hybrid-space data on the k-space data for each channel in all directions in which no undersampling was performed.

13. The method of claim 10, wherein the generating of the channel-by-channel hybrid-space data comprises:
generating the channel-by-channel hybrid-space data by performing an inverse Fourier transform on the k-space data for each channel in a direction in which no undersampling was performed.

14. The method of claim 10, wherein the unitary window has a size determined according to a sensitivity map of each channel of the receiving coil.

15. A computer program for generating a scenario recorded on a non-transitory computer-readable recording medium including computer program instructions executable by a processor, the computer program including instructions for causing a computing device, when executed by a processor of the computing device, to perform steps of receiving, by a receiving coil, an magnetic resonance (MR) signal through a plurality of channels;

generating k-space data for each channel by undersampling the MR signal received from the receiving coil;

generating channel-by-channel hybrid-space data having both a k domain and a spatial domain by performing an inverse Fourier transform on the k-space data for each channel;

reconstructing missing data by applying a parallel image reconstruction, while sliding a unitary window to the channel-by-channel hybrid-space data, within an area corresponding to the unitary window;

generating channel-by-channel MR images by using channel-by-channel reconstructed data; and generating a final MR image based on the channel-by-channel MR images.

* * * * *